US008676832B2

(12) United States Patent
Weese et al.

(10) Patent No.: US 8,676,832 B2
(45) Date of Patent: Mar. 18, 2014

(54) ACCESSING MEDICAL IMAGE DATABASES USING ANATOMICAL SHAPE INFORMATION

(75) Inventors: Juergen Weese, Aachen (DE); Helko Lehmann, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 407 days.

(21) Appl. No.: 12/442,248

(22) PCT Filed: Sep. 26, 2007

(86) PCT No.: PCT/IB2007/053907
§ 371 (c)(1),
(2), (4) Date: Nov. 11, 2009

(87) PCT Pub. No.: WO2008/038233
PCT Pub. Date: Apr. 3, 2008

(65) Prior Publication Data
US 2010/0063977 A1    Mar. 11, 2010

(30) Foreign Application Priority Data

Sep. 29, 2006  (EP) ..................................... 06121512

(51) Int. Cl.
*G06F 7/00*        (2006.01)
(52) U.S. Cl.
USPC ........................................................ 707/769
(58) Field of Classification Search
USPC .......................................... 707/706, 743, 769
See application file for complete search history.

(56) References Cited

U.S. PATENT DOCUMENTS

| | | | |
|---|---|---|---|
| 5,325,297 A * | 6/1994 | Bird et al. ...................... 715/201 |
| 2002/0172406 A1 * | 11/2002 | Rouet et al. ................... 382/128 |
| 2003/0208477 A1 | 11/2003 | Smirniotopoulos et al. | |
| 2007/0276214 A1 * | 11/2007 | Dachille et al. ............... 600/407 |

FOREIGN PATENT DOCUMENTS

| | | |
|---|---|---|
| EP | 1103900 A2 | 5/2001 |
| WO | 0225588 A2 | 3/2002 |

OTHER PUBLICATIONS

El-Kwae et al: "Content-Based Retrieval in Picture Archiving and Communication Systems"; Journal of Digital Imaging, vol. 13, No. 2, May 2000, pp. 70-81.

(Continued)

*Primary Examiner* — Rehana Perveen
*Assistant Examiner* — Hung Havan

(57) ABSTRACT

The invention relates to a system (100) for retrieving a volumetric image data subset comprised in a data storage (105) of volumetric image data sets, the system comprising: a first query unit (111; 113) for composing a first query for searching the data storage (105) for a volumetric image data set comprising the volumetric image data subset; a second query unit (112; 113) for composing a second query for searching the volumetric image data set for the volumetric image data subset, the second query comprising anatomical structure information for identifying an anatomical structure within the volumetric image data set; a first determination unit (121; 123) for determining the volumetric image data set, based on the first query; a second determination unit (122; 123) for determining the volumetric image data subset of the volumetric image data set, based on the anatomical structure identified within the volumetric image data set, using the anatomical structure information comprised in the second query; and a retrieval unit (125) for retrieving the determined volumetric image data subset. The system is thus capable of retrieving a reduced amount of data describing the anatomical structure, i.e. a subset of a volumetric image data set.

19 Claims, 5 Drawing Sheets

(56) References Cited

OTHER PUBLICATIONS

Brown et al: "Database Design and Implementation for Quantitative Image Analysis Research"; IEEE Transactions on Information Technology in Biomedicine, vol. 9, No. 1, Mar. 2005, pp. 99-108.

Muller et al: "The medGIFT Project on Medical Image Retrieval"; University and Hospitals of Geneva, Service of Medical Informatics, 6 Page Document.

Long, et al: "Use of Shape Models to Search Digitized Spine X-Rays"; National Library of Medicine, Bethesda, MD, 6 Page Document.

Mlsna et al: "Intelligent Shape Feature Extraction and Indexing for Efficient Content-Based Medical Image Retrieval"; 6th IEEE Southwest Symposium on Image Analysis and Interpretation, 2004, 5 Page Document.

Flickner et al: "Query by Image and Video Content: The QBIC System"; IBM Almaden Research Center, 1995 IEEE, Sep. 1995, pp. 23-32.

Herve Delingette, "General Object Reconstruction Based on Simplex Meshes", International Journal of Computer Vision, vol. 32, 1999, pp. 111-143.

Thomas Deschamps et al, "Fast Survace and Tree Structure Extraction of Vascular Objects in 3D Medical Images", Curve and Surface Fitting: Saint-Malo, 2002, 10 Pages.

Chris A. Cocosco et al, "A Fully Automatic and Robust Brain MRI Tissue Classification Method", Medical Image Analysis, vol. 7, No. 4, 2003, pp. 513-527.

Hauke Schramm et al, "Towards Fully Automatic Object Detection and Segmentation", Proc. SPIE, vol. 6144, 614402-1, 2006, 10 Pages.

* cited by examiner

ACCESSING MEDICAL IMAGE DATABASES USING ANATOMICAL SHAPE INFORMATION

FIELD OF THE INVENTION

The invention relates to the field of accessing data comprised in medical image databases and more specifically to accessing data comprised in medical image databases, using anatomical shape information.

BACKGROUND OF THE INVENTION

For both diagnosis and therapy planning physicians need to access information comprised in medical image data sets, e.g. Computed Tomography scans, stored in a storage system. A tool for retrieval of medical images stored in a storage system is described in an article by H. Mueller et al entitled "The medGIFT project on medical image retrieval", hereinafter referred to as Ref. 1. The medGIFT tool is strongly based on the GNU Image Finding Tool (GIFT). Like the GIFT, the medGIFT relies on four main groups of features for retrieval: global color features, local color features, global texture features, and local Gabor filter responses. The article also describes different ways of indexing images of lung tissue using clinical information about the contents of images. The article further describes how to remove an image background which does not need to be retrieved. The removal is done by removing specific structures, such as text, followed by a low pass filtering, followed by thresholding and removal of small unconnected objects.

SUMMARY OF THE INVENTION

A limitation of the system described in Ref 1 is that the described system allows removing only a small part of a two-dimensional (2D) image background, typically the logos, the text and the margins. Quite often, especially in the case of three-dimensional (3D) image data sets, the 3D image data set comprises a plurality of anatomical structures. However, the physician may be interested in retrieving an anatomical structure of interest comprised in the 3D image data set and may not be interested in retrieving another anatomical structure comprised in the 3D image data.

It would be advantageous to have a system for retrieving data describing an anatomical structure of interest and being comprised in a volumetric image data set, said system being capable of reducing the necessary amount of data to be transferred from a data storage to a memory unit and/or to a processor of the system.

To address this issue, in an aspect of the invention, a system for retrieving a volumetric image data subset comprised in a data storage of volumetric image data sets comprises:

a first query unit for composing a first query for searching the data storage for a volumetric image data set comprising the volumetric image data subset;

a second query unit for composing a second query for searching the volumetric image data set for the volumetric image data subset, the second query comprising anatomical structure information for identifying an anatomical structure within the volumetric image data set;

a first determination unit for determining the volumetric image data set, based on the first query;

a second determination unit for determining the volumetric image data subset of the volumetric image data set, based on the anatomical structure identified within the volumetric image data set using the anatomical structure information comprised in the second query; and a retrieval unit for retrieving the determined volumetric image data subset.

The first determination unit is arranged to determine the volumetric image data set based on the first query, e.g. based on the patient's name, on the image acquisition modality, and on the date of image acquisition comprised in the first query. The anatomical structure comprised in the volumetric image data set may be identified using image data segmentation, and segmentation results may be stored in the data storage. Optionally, the system may be arranged to segment the volumetric image data set and to identify the anatomical structure comprised in the volumetric image data set based on the segmentation results and on the anatomical structure information comprised in the second query. The second determination unit may be arranged to access segmentation results, based on the anatomical structure information comprised in the second query, and to determine the volumetric image data subset as a subset comprising data elements comprised in the identified anatomical structure. The retrieval unit may be arranged to retrieve these data elements, thereby retrieving the subset of the volumetric image data set comprising the anatomical structure. The system is thus capable of retrieving a reduced amount of data describing the anatomical structure, i.e. a subset of a volumetric image data set.

In an embodiment of the system, the system further comprises an addition unit for adding a new volumetric image data set to the data storage. The addition unit allows a user to add the new volumetric image data set, e.g. a volumetric image data set comprising a thoracic CT scan of a new patient, to the data storage. A subset of the new volumetric image data set may be retrieved when the subset is needed by a physician for diagnosis or as a reference.

In an embodiment of the system, the system further comprises a segmentation unit for segmenting the volumetric image data set, based on the anatomical structure information. For example, the segmentation unit may be implemented as an adaptation unit for adapting a shape model described in the anatomical structure information to the anatomical structure within the volumetric image data set determined by the first determination unit. A suitable adaptation method is described in an article by H. Schramm et al., entitled "Toward fully automatic object detection and segmentation" in Proc. SPIE Vol. 6144, 614402; Medical Imaging 2006: Image Processing; J. M. Reinhardt, J. P. Pluim; Eds., pages 11-20, hereinafter referred to as Ref 2. The adapted shape model allows identifying the anatomical structure. Including the segmentation unit in the system advantageously allows the system to identify anatomical structure within the volumetric image data set, using image data segmentation, e.g. shape model adaptation.

In an embodiment of the system, the system is further arranged to identify the anatomical structure in the new volumetric image data set, based on the anatomical structure information, when the new volumetric image data set is added to the data storage. The anatomical structure information from old queries may be stored by the system or may be provided, by the user, with the new volumetric image data set. When the user adds a new volumetric image data set, the system may be arranged to segment the new volumetric image data set in order to identify the anatomical structure in the new volumetric image data set, based on said anatomical structure information. To this end, the system may be arranged to employ the segmentation unit. A description of the anatomical structure, e.g. coordinates of vertices of a cuboid or coordinates of vertices of a triangular mesh adapted to the anatomical structure, comprising locations of data elements of the anatomical structure, may be stored in the data storage with the volumetric image data set. This description of the anatomical structure may be used later, during data retrieval, by the second determination unit to determine the volumetric image data subset comprising the anatomical structure. Identifying the anatomical structure in the new volumetric image data set when the new volumetric image data set is added to the data storage advantageously accelerates determining and retrieving the volumetric image data subset.

In an embodiment of the system, the second determination unit is arranged to determine the volumetric image data subset, based on a shape model adapted to the anatomical structure within the volumetric image data set. An exemplary shape model comprises a triangular mesh for modeling the surface of the anatomical structure. The segmentation unit of the system may be arranged to adapt the triangular mesh to the anatomical structure within the volumetric image data set, determined by the first determination unit. Alternatively, the shape model may be already adapted to the anatomical structure within the volumetric image data set, determined by the first determination unit. The adapted triangular mesh allows identifying locations comprised in a volume bounded by the adapted triangular mesh modeling the surface of the anatomical structure. Data elements comprising these locations may be determined by the second determination unit as data elements comprised in the volumetric image data subset. Determining the volumetric image data subset, based on the adapted model mesh allows minimizing the size of the volumetric image data subset.

In an embodiment of the system, the anatomical structure information further comprises information on a property of the anatomical structure. The property may further describe the anatomical structure, e.g. the size and shape of the anatomical structure such as a lung nodule. This enables the user to retrieve nodules which, for example, are larger than a reference ellipsoid.

In an embodiment of the system, the retrieval unit is further arranged for retrieving a characteristic of the determined volumetric image data subset. The second query anatomical structure information may further comprise a request for retrieving a characteristic of the determined volumetric image data subset. The characteristic may be, for example, coordinates of vertices of a triangular mesh adapted to the anatomical structure comprised in the determined volumetric image data subset or a binary mask describing data elements of the anatomical structure comprised in the determined volumetric image data subset. The retrieved characteristic, e.g. coordinates of vertices of a triangular mesh adapted to the anatomical structure comprised in the determined volumetric image data subset, may be used for further analysis of the anatomical structure. Retrieving coordinates of vertices of a triangular mesh adapted to the anatomical structure eliminates the need for adapting the triangular mesh model to the anatomical structure comprised in the determined volumetric image data subset.

In an embodiment of the system, the system further comprises a client unit comprising the first query unit and the second query unit, and a server unit comprising the data storage, the first determination unit, and the second determination unit. The server unit may be connected to a plurality of client units via a computer network such as local area network, metropolitan area network, world area network, etc. This allows a plurality of users to have concurrent access to the data storage from a plurality of locations.

In a further aspect of the invention, the system according to the invention is comprised in an image acquisition apparatus.

In a further aspect of the invention, the system according to the invention is comprised in a workstation.

In a further aspect of the invention, a method of retrieving a volumetric image data subset comprised in a data storage of volumetric image data sets comprises:

a first query step for composing a first query for searching the data storage for a volumetric image data set comprising the volumetric image data subset;

a second query step for composing a second query for searching the volumetric image data set for the volumetric image data subset, the second query comprising anatomical structure information for identifying an anatomical structure within the volumetric image data set;

a first determination step for determining the volumetric image data set, based on the first query;

a second determination step for determining the volumetric image data subset of the volumetric image data set, based on the anatomical structure identified within the volumetric image data set, using the anatomical structure information comprised in the second query; and a retrieval step for retrieving the determined volumetric image data subset.

In a further aspect of the invention, a computer program product to be loaded by a computer arrangement comprises instructions for retrieving a volumetric image data subset comprised in a data storage of volumetric image data sets, the computer arrangement comprising a processing unit and a memory, the computer program product, after being loaded, providing said processing unit with the capability to carry out the following tasks:

composing a first query for searching the data storage for a volumetric image data set comprising the volumetric image data subset;

composing a second query for searching the volumetric image data set for the volumetric image data subset, the second query comprising anatomical structure information for identifying an anatomical structure within the volumetric image data set;

determining the volumetric image data set, based on the first query;

determining the volumetric image data subset of the volumetric image data set, based on the anatomical structure identified within the volumetric image data set, using the anatomical structure information comprised in the second query; and retrieving the determined volumetric image data subset.

Modifications and variations thereof, of the image acquisition apparatus, of the workstation, of the method, and/or of the computer program product, which correspond to modifications of the system and variations thereof, as described herein, can be carried out by a skilled person on the basis of the present description.

The skilled person will appreciate that the method may be applied to volumetric, i.e. three-dimensional (3D) and four-dimensional (4D) image data acquired by various acquisition modalities such as, but not limited to, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention will become apparent from and will be elucidated with respect to the implementations and embodiments described hereinafter and with reference to the accompanying drawings, wherein.

The same reference numerals are used to denote similar parts throughout the Figures.

DETAILED DESCRIPTION OF EMBODIMENTS

Figure 1A:
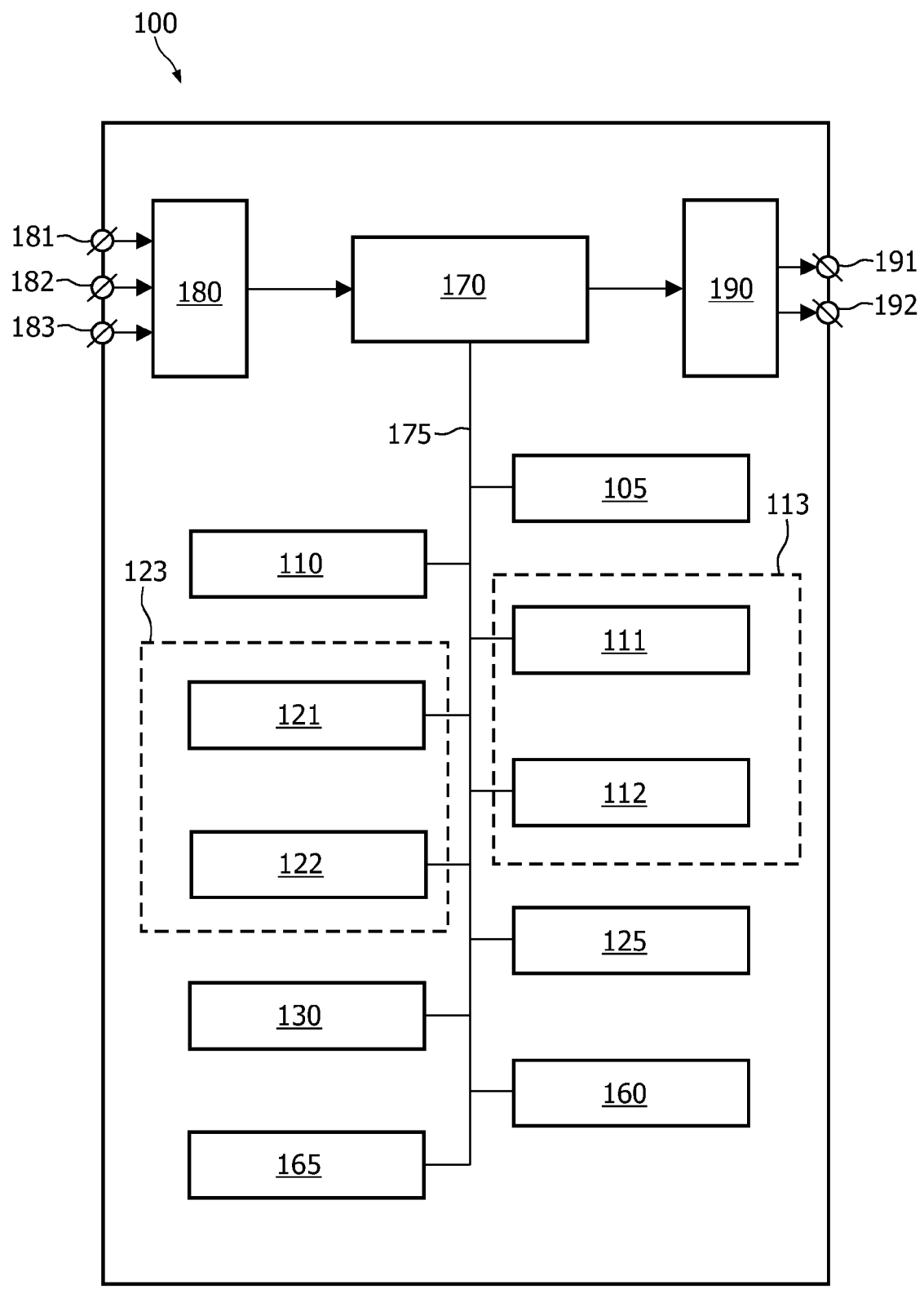
FIG. 1A schematically shows a block diagram of an exemplary embodiment of the system.

FIG. 1 schematically shows a block diagram of an exemplary embodiment of the system 100 for retrieving a volumetric image data subset comprised in a data storage 105 of volumetric image data sets, the system comprising:

a first query unit 111 for composing a first query for searching the data storage 105 for a volumetric image data set comprising the volumetric image data subset;

a second query unit 112 for composing a second query for searching the volumetric image data set for the volumetric image data subset, the second query comprising anatomical structure information for identifying an anatomical structure within the volumetric image data set;

a first determination unit 121 for determining the volumetric image data set, based on the first query;

a second determination unit 122 for determining the volumetric image data subset of the volumetric image data set, based on the anatomical structure identified within the volumetric image data set, using the anatomical structure information comprised in the second query; and a retrieval unit 125 for retrieving the determined volumetric image data subset.

The exemplary embodiment of the system 100 further comprises the following optional units:

an addition unit 110 for adding a new volumetric image data set to the data storage 105;

a segmentation unit 130 for segmenting the volumetric image data set, based on the anatomical structure information;

a control unit 160 for controlling the workflow in the system 100;

a user interface 165 for communicating with a user of the system 100; and a memory unit 170 for storing data.

In an embodiment of the system 100, there are three input connectors 181, 182 and 183 for the incoming data. The first input connector 181 is arranged to receive data coming in from a data storage such as, but not limited to, a hard disk, a magnetic tape, a flash memory, or an optical disk. The second input connector 182 is arranged to receive data coming in from a user input device such as, but not limited to, a mouse or a touch screen. The third input connector 183 is arranged to receive data coming in from a user input device such as a keyboard. The input connectors 181, 182 and 183 are connected to an input control unit 180.

In an embodiment of the system 100, there are two output connectors 191 and 192 for the outgoing data. The first output connector 191 is arranged to output the data to a data storage such as a hard disk, a magnetic tape, a flash memory, or an optical disk. The second output connector 192 is arranged to output the data to a display device. The output connectors 191 and 192 receive the respective data via an output control unit 190.

The skilled person will understand that there are many ways to connect input devices to the input connectors 181, 182 and 183 and the output devices to the output connectors 191 and 192 of the system 100. These ways comprise, but are not limited to, a wired and a wireless connection, a digital network such as, but not limited to, a Local Area Network (LAN) and a Wide Area Network (WAN), the Internet, a digital telephone network, and an analogue telephone network.

In an embodiment of the system 100, the system 100 comprises a memory unit 170. The system 100 is arranged to receive input data from external devices via any of the input connectors 181, 182, and 183 and to store the received input data in the memory unit 170. Loading the input data into the memory unit 170 allows quick access to relevant data portions by the units of the system 100. The input data may comprise, for example, a user input for composing the first query and the second query. Optionally, the input data may comprise a new volumetric image data set for adding to the data storage 105. The memory unit 170 may be implemented by devices such as, but not limited to, a Random Access Memory (RAM) chip, a Read Only Memory (ROM) chip, and/or a hard disk drive and a hard disk. The memory unit 170 may be further arranged to store the output data. The output data may comprise, for example, the retrieved volumetric image data subset. The memory unit 170 is also arranged to receive data from and deliver data to the units of the system 100 comprising the data storage 105, the addition unit 110, the first query unit 111, the second query unit 112, the first determination unit 121, the second determination unit 122, the retrieval unit 125, the segmentation unit 130, the control unit 160, and the user interface 165, via a memory bus 175. The memory unit 170 is further arranged to make the output data available to external devices via any of the output connectors 191 and 192. Storing the data from the units of the system 100 in the memory unit 170 may advantageously improve the performance of the units of the system 100 as well as the rate of transfer of the output data from the units of the system 100 to external devices.

Alternatively, the system 100 may not comprise the memory unit 170 and the memory bus 175. The input data used by the system 100 may be supplied by at least one external device, such as an external memory or a processor, connected to the units of the system 100. Similarly, the output data produced by the system 100 may be supplied to at least one external device, such as an external memory or a processor, connected to the units of the system 100. The units of the system 100 may be arranged to receive the data from each other via internal connections or via a data bus.

In an embodiment of the system 100, the system 100 comprises a control unit 160 for controlling the workflow in the system 100. The control unit may be arranged to receive control data from and provide control data to the units of the system 100. For example, after determining the volumetric image data set, the first determination unit 121 may be arranged to send a control data "the volumetric image data set is determined" to the control unit 160 and the control unit 160 may be arranged to provide a control data "segment the anatomical structure in the volumetric image data set" to the segmentation unit 130, requesting the segmentation unit 130 to segment the volumetric image data set and to identify the anatomical structure within the volumetric image data set, based on the anatomical structure information comprised in the second query. Alternatively, a control function may be implemented in another unit of the system 100.

In an embodiment of the system 100, the system 100 comprises a user interface 165 for communicating with the user of the system 100. The user interface 165 may be arranged to provide the user with means for entering a first query input and a second query input. Optionally, the user interface may receive a user input for selecting a mode of operation of the system 100 such as a mode for selecting a method for segmenting the volumetric image data set by the segmentation unit 130 in order to identify an anatomical structure within the volumetric image data set. The skilled person will understand that more functions may be advantageously implemented in the user interface 165 of the system 100.

A volumetric, i.e. three-dimensional (3D), image data set comprises elements. Each data element (x, y, z, I) of the volumetric image data comprises a location (x, y, z), typically represented by three Cartesian coordinates x, y, z in an image data set coordinate system, and an intensity I at this location. The medical image data volume may be defined as a volume comprising all locations (x, y, z) comprised in the image data elements (x, y, z, I). The volumetric image data set may be organized as a collection of substantially planar sections of the image volume, e.g. sections substantially perpendicular to a z axis of the coordinate system. A 4D image data set comprises a collection of volumetric image data sets acquired at different time instances or at different phases of motion.

Volumetric image data sets are stored in the data storage 105 of the system 100. The data storage 105 is a permanent, i.e. non-volatile, storage device, which allows to store, to read, and to write digitized data. Such storage devices may use magnetic discs, optical discs, and/or magnetic tapes, for example. The skilled person will know useful ways of implementing the data storage 105.

In an embodiment of the system 100, the system comprises an addition unit 110 for adding a new volumetric image data set to the data storage 105. When a new volumetric image data set is acquired by an acquisition apparatus, the system 100 may obtain this new volumetric image data set for storing it. For example, the new volumetric image data set may be transferred to the system memory unit 170 via a computer network. The addition unit 110 is arranged to put the new volumetric image data set from the memory unit 170 into the data storage 105. The addition unit may be further arranged to put reference information on the new volumetric image data set into the data storage. The reference information may comprise a description of the volumetric image data set and an address of the volumetric image data set in the data storage. The description of the volumetric image data set may comprise a name of a patient and, optionally, further information about the patient, an image data acquisition modality, a date of data acquisition, and a description of contents of the volumetric image data set, e.g. a list of anatomical structures identified in the volumetric image data set. The system 100 may be arranged to obtain the reference information from a user input and/or from a metadata associated with the new volumetric image data set. Optionally, the system 100 may be arranged to derive a part of the reference information from the new volumetric image data set, e.g. by segmenting the volumetric image data. The address of the volumetric image data set may be a memory address, where the digitized volumetric image data set is written on a magnetic disk. Alternatively, the address of the volumetric image data set may be a memory address of a record comprising the address of the digitized volumetric image data set in the data storage. The reference information may be stored in a relational database, for example. The volumetric image data set may be determined based on the reference information.

The first query unit 111 of the system 100 is arranged to compose a first query for searching the data storage 105 for a volumetric image data set comprising the volumetric image data subset. The user may provide an input necessary for composing the first query, using the user interface 165. The user input may comprise, for example, a name of a patient, e.g. John Smith, an image data acquisition modality, e.g. X-ray CT, and a date of data acquisition, e.g. Oct. 7, 2006. This query describes most likely one volumetric image data set. Alternatively, the query may comprise the sex of a patient, e.g. male, an image acquisition modality, e.g. MRI, and a name of an anatomical structure to be comprised in the volumetric image data set, e.g. right coronary artery tree. This query is likely to describe a plurality of volumetric image data sets. The user interface may be arranged to assist the user in entering the user input for composing the first query. For example, the user interface may comprise means such as, but not limited to, a patient name textbox and a button for guiding the user in entering the user input for composing the first query. The first query composed by the first unit is used to search for the volumetric image data set, based on reference information of the data set.

The second query unit 112 of the system 100 is arranged to compose a second query for searching the volumetric image data set for the volumetric image data subset, the second query comprising anatomical structure information for identifying an anatomical structure within the volumetric image data set. The anatomical structure may be, for example, a cardiac structure, a lung structure, a colon structure, a bone, an artery tree, or a structure in the brain. The user may provide an input necessary for composing the query, using the user interface 165. The user input may comprise, for example, a name of an anatomical structure comprised within the volumetric image data set. The user input may further comprise information on how to identify the anatomical structure, e.g. by adapting a shape model to the anatomical structure comprised in the volumetric image data set or by accessing a list of anatomical structures identified in the volumetric image data set. The second query unit 112 is arranged to compose the second query, based on the user input. The second query may comprise the name of the anatomical structure comprised in the user input. The second query may further comprise the information on the shape model for adapting to the anatomical structure comprised in the volumetric image data set. The shape model information may comprise a link for obtaining the shape model. Alternatively, the shape model information may comprise a description of the shape model for use by the determination unit.

The skilled person will understand that the first query unit 111 and the second query unit 112 may be implemented as one query unit 113 for composing one query comprising the first query and the second query. The user interface 165 may comprise means that assist the user in creating syntactically correct queries.

The first determination unit 121 of the system 100 is arranged to determine the volumetric image data set, based on the first query. Determining the volumetric image data set by the first determination unit 121 should be interpreted as determining an access to the volumetric image data set by the second determination unit 122, i.e. making the data comprised in the volumetric image data set available to the second determination unit 122. For example, determining the volumetric image data set by the first determination unit 121 may involve searching and finding an address of the volumetric image data in the data storage. Determining the volumetric image data set by the first determination unit 121 may further involve creating a copy of the volumetric image data set in the memory unit 170 of the system 100.

Determining the volumetric image data set may begin after the first query is available and before the second query is composed. The first determination unit 121 may be arranged to search the database comprising the volumetric image data set reference information. In an embodiment of the system 100, the first determination unit 121 finds the reference information of the volumetric image data set, comprising a memory address of the volumetric image data set. The first determination unit is further arranged to pass this address to the second determination unit 122 of the system 100. The first determination unit may be further arranged to pass a clue extracted from the reference information to the second query unit 112 and also to the user interface 165 in order to better assist the user in creating a semantically correct second query. For example, the clue extracted from the reference information may comprise a list of anatomical structures comprised in the volumetric image data set or a list of volumetric image data sets satisfying the first query. The user may further refine the first query to determine the volumetric image data set.

The second determination unit 122 of the system 100 is arranged to determine the volumetric image data subset of the volumetric image data set, based on the anatomical structure identified within the volumetric image data set, using the anatomical structure information comprised in the second query. Determining the volumetric image data set by the second determination unit 122 should be interpreted as determining an access to the volumetric image data subset by the retrieval unit 125, i.e. making the data comprised in the volumetric image data subset available to the retrieval unit 125. For example, determining the volumetric image data subset by the second determination unit 122 may involve searching and finding data elements, which locations are comprised in a mesh adapted to said anatomical structure or in a cuboid comprising said mesh. Determining the volumetric image data set by the second determination unit 122 may further involve creating a copy of the volumetric image data subset in the memory unit 170 of the system 100.

In an embodiment of the system 100, the second determination unit 122 uses the anatomical structure information comprised in the second query to search the reference information of the volumetric image data set for clues about anatomical structures comprised in the volumetric image data set. For example, the reference information may comprise a list of anatomical structures comprised in the volumetric image data set. For each anatomical structure listed in the reference information, the list may also comprise a respective cuboid comprising a volume of said anatomical structure. The second determination unit may be arranged to find the name of the anatomical structure in the list and, consequently, to determine the cuboid comprising the anatomical structure. Data elements whose locations are comprised in the cuboid may be the data elements of the determined volumetric image data subset.

If the first determination unit 121 fails to determine the volumetric image data set, based on the first query, or if the second determination unit 122 fails to determine the subset of the volumetric image data set, using the anatomical structure information comprised in the second query, then the control unit 160 may be arranged to obtain a "failed" input from the respective determination unit and to execute a default "failed" action, e.g. the control unit may request the user interface 165 to display a message "no volumetric image data set matches your first query" or "no volumetric image data subset matches your second query".

The skilled person will understand that the first determination unit 121 and the second determination unit 122 may be implemented as one determination unit 123 for determining the volumetric image data subset of the volumetric image data set, based on the first query and on the second query.

In an embodiment of the system 100, the second determination unit 122 is arranged to determine the volumetric image data subset, based on a shape model adapted to the anatomical structure within the volumetric image data set. The volumetric image data subset comprises data elements with locations inside a model mesh adapted to the anatomical structure. The model mesh may have been adapted to the anatomical structure within the volumetric image data set when the volumetric image data set was added to the data storage. Vertex coordinates of the adapted model mesh in the volumetric image data set coordinate system may be stored in the reference information of the volumetric image data set. The second query may comprise anatomical structure information comprising the name of the anatomical structure. The name of the anatomical structure may be used by the second determination unit 122 to obtain vertex coordinates of the model mesh adapted to the anatomical structure. The vertex coordinates of the adapted model mesh are used by the second determination unit 122 to determine data elements of the volumetric image data set. The volumetric image data subset comprises these data elements, which are located inside the volume bounded by the model mesh.

Optionally, the anatomical structure information may comprise information on a shape model for adapting to the anatomical structure and a unit of the system 100. For example, the segmentation unit 130 may comprise a description of the shape model to be adapted to the anatomical structure. The second determination unit 122 may employ the segmentation unit 130 to adapt the anatomical structure within the volumetric image data set.

The retrieval unit 125 of the system 100 is arranged to retrieve the volumetric image data subset. The volumetric image data subset may be loaded into the memory unit 170 of the system 100. The user may use other viewing and/or analytic applications to view and/or extract more information form the volumetric image data subset. Optionally, a viewing and/or analytic application may be implemented in a further unit of the system 100.

In an embodiment of the system 100, the system 100 further comprises a segmentation unit 130 for segmenting the anatomical structure within the volumetric image data set, based on the anatomical structure information. Segmenting the volumetric image data set may be accomplished in many ways, such as, but not limited to, segmentation using detection-ray casting with profile matching, segmentation using shape models, segmentation using wave-front propagation, and segmentation using voxel classifiers. Optionally, segmenting the volumetric image data set, based on the anatomical structure information, may be carried out interactively, with a participation of the user. Segmenting the volumetric image data set may be carried out just before retrieving the volumetric image data subset or at any other time prior to retrieving the volumetric image data subset. The results of the segmentation, in particular an anatomical structure identified during the segmentation, may be stored with the volumetric image data set for future use. In an embodiment, the segmentation unit 130 may be a stand-alone unit of the system 100 or may be also a unit of another system.

In an embodiment of the system 100, the segmentation unit 130 is arranged to adapt a shape model comprising a triangular mesh to the anatomical structure within the volumetric image data set, determined by the first determination unit. The triangular mesh may be determined by the segmentation unit 130, based on the anatomical structure information. For example, the triangular mesh may be described in the anatomical structure information. The triangular mesh describes the surface of the anatomical structure to which it was adapted. A suitable adaptation method for adapting triangular meshes is described in Ref. 2.

In an embodiment of the system 100, the segmentation unit 130 is arranged to adapt a simplex mesh of the shape model to the anatomical structure within the volumetric image data set. The simplex mesh describes the surface of the anatomical structure to which it was adapted. The simplex mesh may be determined by the segmentation unit 130, based on the anatomical structure information. For example, a description of the simplex mesh may be comprised in the segmentation unit 130. Image segmentation based on adapting simplex meshes to anatomical structures in a medical image data is described in an article by H. Delingette, entitled "General Object Reconstruction based on Simplex Meshes" in International Journal of Computer Vision, vol. 32, pages 11-142, 1999.

In an embodiment of the system 100, the segmentation unit 130 is arranged to employ a wave-front propagation method to segment the volumetric image data set. Values of initialization parameters necessary for wave-front propagation may be comprised in the anatomical structure information. For example, identifying a coronary artery using wave-front propagation is described in an article by T. Deschamps and L. D. Cohen, entitled "Fast Surface and Tree Structure Extraction of Vascular Objects in 3D medical objects" in Curve and Surface Design, Saint-Malo 2002, T. Lyche, M.-L. Mazure, and L. L. Schumaker, Eds., Nashboro Press, Brentwood, 2003.

In an embodiment of the system 100, the segmentation unit 130 is arranged to employ a data classifier for classifying elements of the volumetric image data set as elements comprised in the anatomical structure or as elements not comprised in the anatomical structure. The data classifier may be determined by the segmentation unit 130, based on the anatomical structure information. For example, a data classifier definition or a link to a data classifier definition, which allows the segmentation unit 130 to use said data classifier, may be comprised in the anatomical structure information. Classification of data elements in a Magnetic Resonance brain image data set is described in an article by C. A. Cocosco et al, entitled "A Fully Automatic and Robust Brain MRI Tissue Classification Method" in Medical Image Analysis, vol. 7, pages 513-527, 2003.

In an embodiment of the system 100, the system 100 is further arranged to identify the anatomical structure in the new volumetric image data set, based on the anatomical structure information, when the new volumetric image data set is added to the data storage 105. When a new volumetric image data is added to the data storage 105, a set of standard queries comprising anatomical structure information for identifying common anatomical structures may be used to segment the volumetric image data set in order to identify common anatomical structures in the new volumetric image data set. The set of standard queries may be stored in the system 100. Information about the common anatomical structures identified in the new volumetric image data set, e.g. vertex coordinates of a model mesh adapted to a common anatomical structure, may be stored in the reference information on the new volumetric image data set.

In an embodiment of the system 100, the anatomical structure information further comprises information on a property of the anatomical structure. The information on a property of the anatomical structure may be information about a problem with the anatomical structure, e.g. about bone mineral density, the so-called T-score, used to determine the severity of osteoporosis, or a size of the anatomical structure. The second determination unit may comprise means to compute the property of the anatomical structure comprised in the determined volumetric image data subset. Optionally, the reference information of the determined volumetric image data set may comprise information on the property of the anatomical structure comprised in the volumetric image data set.

In an embodiment of the system 100, the first query may be designed for determining a plurality of volumetric image data sets, e.g. a collection of sequences of temporally acquired volumetric image data sets of the heart. The second query may be designed for determining a property of a sequence of volumetric image data sets, e.g. ejection fraction of the heart. The system 100 may be arranged to retrieve an end-diastole volumetric image data subset for imaging the heart and an end-systole volumetric image data subset for imaging the heart, comprised in a sequence with an abnormal, e.g. less than 55%, ejection fraction.

In an embodiment of the system, the retrieval unit 125 is further arranged for retrieving a characteristic of the determined volumetric image data subset. The second query anatomical structure information may further comprise a request for retrieving a characteristic of the determined volumetric image data subset. The characteristic may be, for example, coordinates of vertices of a triangular mesh adapted to the anatomical structure comprised in the determined volumetric image data set or a binary mask describing the data elements of the anatomical structure comprised in the determined volumetric image data set. The retrieved characteristic, e.g. coordinates of vertices of a triangular mesh adapted to the anatomical structure comprised in the determined volumetric image data set, may be used for further analysis of the anatomical structure.

The skilled person will appreciate that it is possible to combine a few embodiments of the system 100. For example, it is possible that the second determination unit 122 checks the reference information of the volumetric image data set for clues about the identified anatomical structure. If the reference information comprises a description of a polygonal mesh adapted to the anatomical structure within the volumetric image data set, the description of the polygonal mesh may be used to determine the volumetric image data subset, based on the adapted polygonal mesh. If the reference information does not comprise clues about the identified anatomical structure, the second determination unit 122 may be arranged to employ the segmentation unit 130 to segment the volumetric image data in order to identify the anatomical structure, e.g. for adapting a polygonal mesh to the anatomical structure within the volumetric image data set.

Figure 1B:
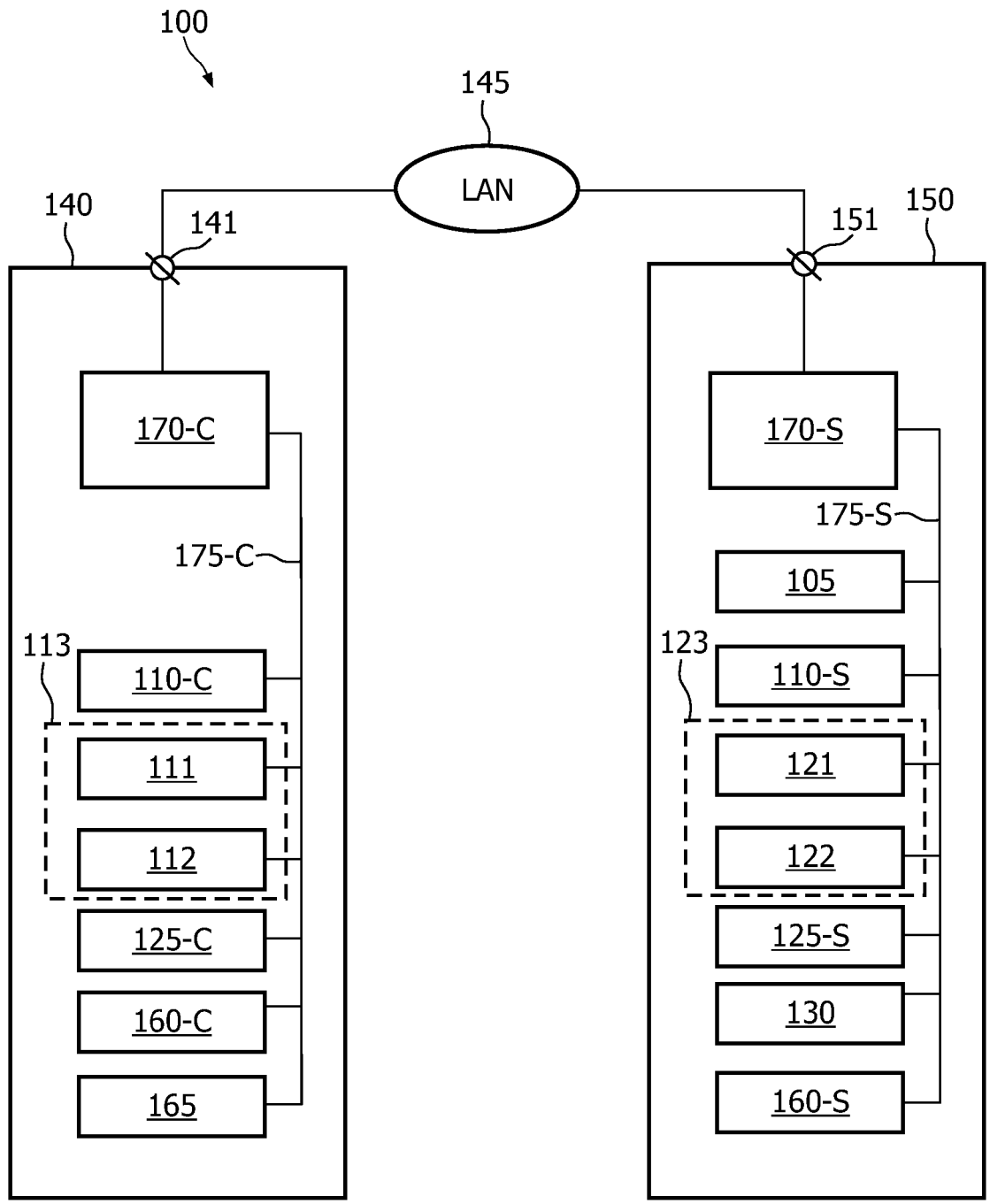
FIG. 1B schematically shows a block diagram of a further exemplary embodiment of the system based on client-server architecture.

FIG. 1B schematically shows a block diagram of a further exemplary embodiment of the system 100 based on client-server architecture. In this embodiment the system 100 further comprises a client unit 140 comprising the first query unit 111 and the second query unit 112, and a server unit 150 comprising the data storage 105, the first determination unit 121, and the second determination unit 122. The first query unit 112 and the second query unit may be implemented as one query unit 113. The first determination unit 121 and the second determination unit 122 may be implemented as one determination unit 123. Both the client unit 140 and the server unit 150 are connected to a network such as, but not limited to, a LAN 145 via I/O connectors 141 and 151, respectively. The client unit 140 further comprises the client-part of the addition unit 110-C, the client-part of the retrieval unit 125-C, the client-part of the control unit 160-C, the user interface 165, the client memory unit 170-C and the client data bus 175-C. The server unit 150 further comprises the server-part of the addition unit 110-S, the server-part of the retrieval unit 125-S, the segmentation unit 130, the server-part of the control unit 160-S, the server memory unit 170-S and the server data bus 175-S.

The skilled person will understand that other embodiments of the system 100 are also possible. It is possible, among other things, to redefine the units of the system and to redistribute their functions. For example, in an embodiment of the system 100, the functions of the segmentation unit 130 may be combined with the functions of the second determination unit 122. In a further embodiment of the system 100, there can be a plurality of segmentation units replacing the segmentation unit 130. Each segmentation unit of the plurality of segmentation units may be arranged to employ a different segmentation method for identifying an anatomical structure. The employed segmentation method may be based on a user selection comprised in the second query.

The units of the system 100 may be implemented using a processor. Normally, their functions are performed under the control of a software program product. During execution, the software program product is normally loaded into a memory, like a RAM, and executed from there. The program may be loaded from a background memory, like a ROM, hard disk, or magnetic and/or optical storage, or may be loaded via a network like the Internet. Optionally, an application specific integrated circuit may provide the described functionality.

Figure 2:
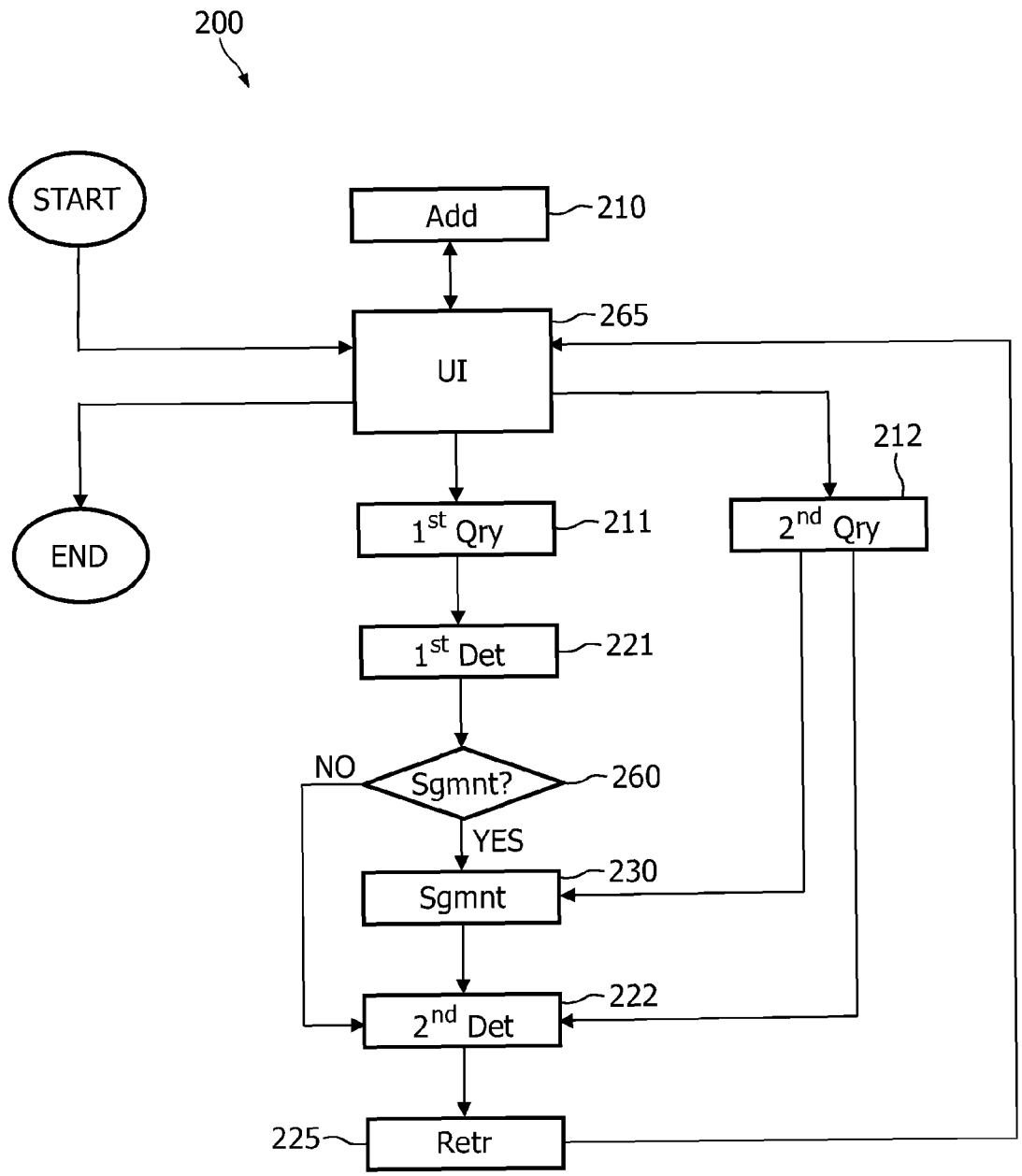
FIG. 2 shows a flowchart of an exemplary implementation of the method.

FIG. 2 shows a flowchart of an exemplary implementation of the method 200 of retrieving a volumetric image data subset comprised in a data storage of volumetric image data sets. The method 200 begins with a UI step 265 for receiving a user input. After receiving the user input for adding a new volumetric image data set to the data storage, the method 200 continues to an addition step 210 for adding a new volumetric image data set to the data storage. After the addition step 210 the method returns to the UI step 265. After receiving the user input for retrieving a subset of a volumetric image data set, the method continues to a first query step 211 for composing a first query for searching the data storage for a volumetric image data set comprising the volumetric image data subset. Concurrently, the method 200 continues to a second query step 212 for composing a second query for searching the volumetric image data set for the volumetric image data subset, the second query comprising anatomical structure information for identifying an anatomical structure within the volumetric image data set. After the first query step 211 the method continues to a first determination step 221 for determining the volumetric image data set based on the first query. After the first determining step 221 the method continues to a control step 260 for controlling the flow of the method 200. If the anatomical structure within the volumetric image data set needs to be identified, the method continues to a segmentation step 230 for segmenting the volumetric image data set and identifying the anatomical structure within the volumetric image data set, based on the anatomical structure information. After the segmentation step 230 the method continues to a second determination step 222 for determining the volumetric image data subset of the volumetric image data set, based on the anatomical structure identified within the volumetric image data set, using the anatomical structure information comprised in the second query. If the volumetric image data set does not need to be segmented the method jumps from the control step 260 to said second determination step 222. After the second determination step 222 the method continues to a retrieval step 225 for retrieving the determined volumetric image data subset. After the retrieval step the method returns to the UI step 265. After receiving the user input for terminating the method 200, the method 200 terminates.

The order of steps in the method 200 is not mandatory, the skilled person may change the order of some steps or perform some steps concurrently using threading models, multi-processor systems or multiple processes without departing from the concept as intended by the present invention. Optionally, two or more steps of the method 200 of the current invention may be combined into one step. Optionally, a step of the method 200 of the current invention may be split into a plurality of steps.

Figure 3:
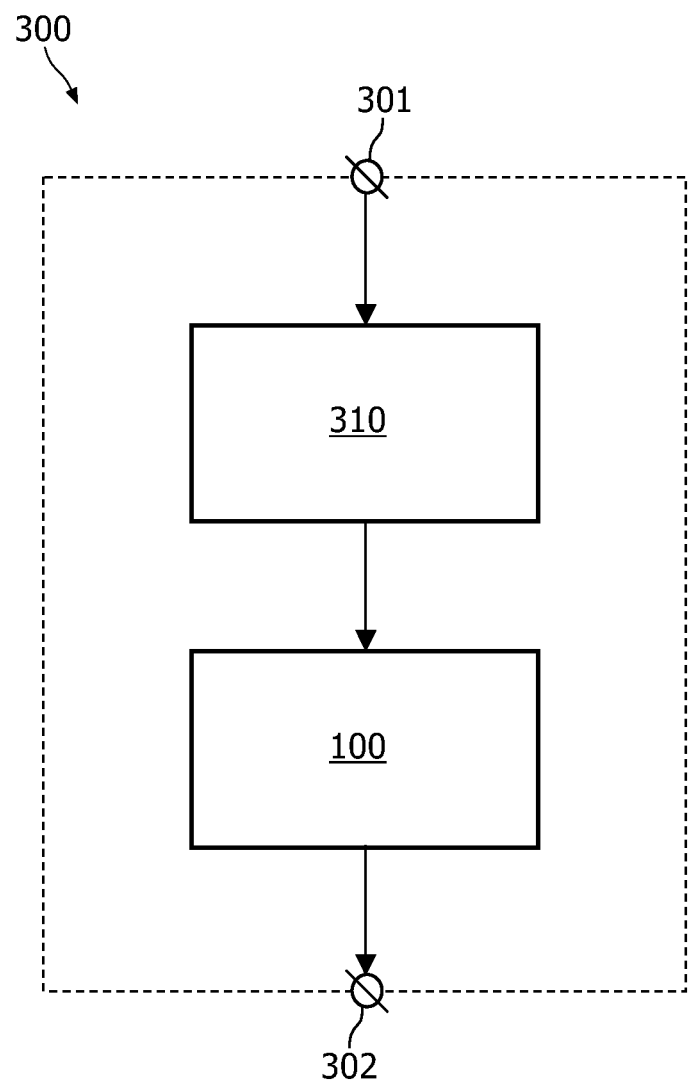
FIG. 3 schematically shows an exemplary embodiment of the image acquisition apparatus.

FIG. 3 schematically shows an exemplary embodiment of the image acquisition apparatus 300 employing the system 100, said image acquisition apparatus 300 comprising an image acquisition unit 310 connected via an internal connection with the system 100, an input connector 301, and an output connector 302. This arrangement advantageously increases the capabilities of the image acquisition apparatus 300, providing said image acquisition apparatus 300 with advantageous capabilities of the system 100 for retrieving a volumetric image data subset comprised in a data storage of volumetric image data sets. Examples of image acquisition apparatus comprise, but are not limited to, a CT system, an X-ray system, an MRI system, a US system, a PET system, a SPECT system, and a NM system.

Figure 4:
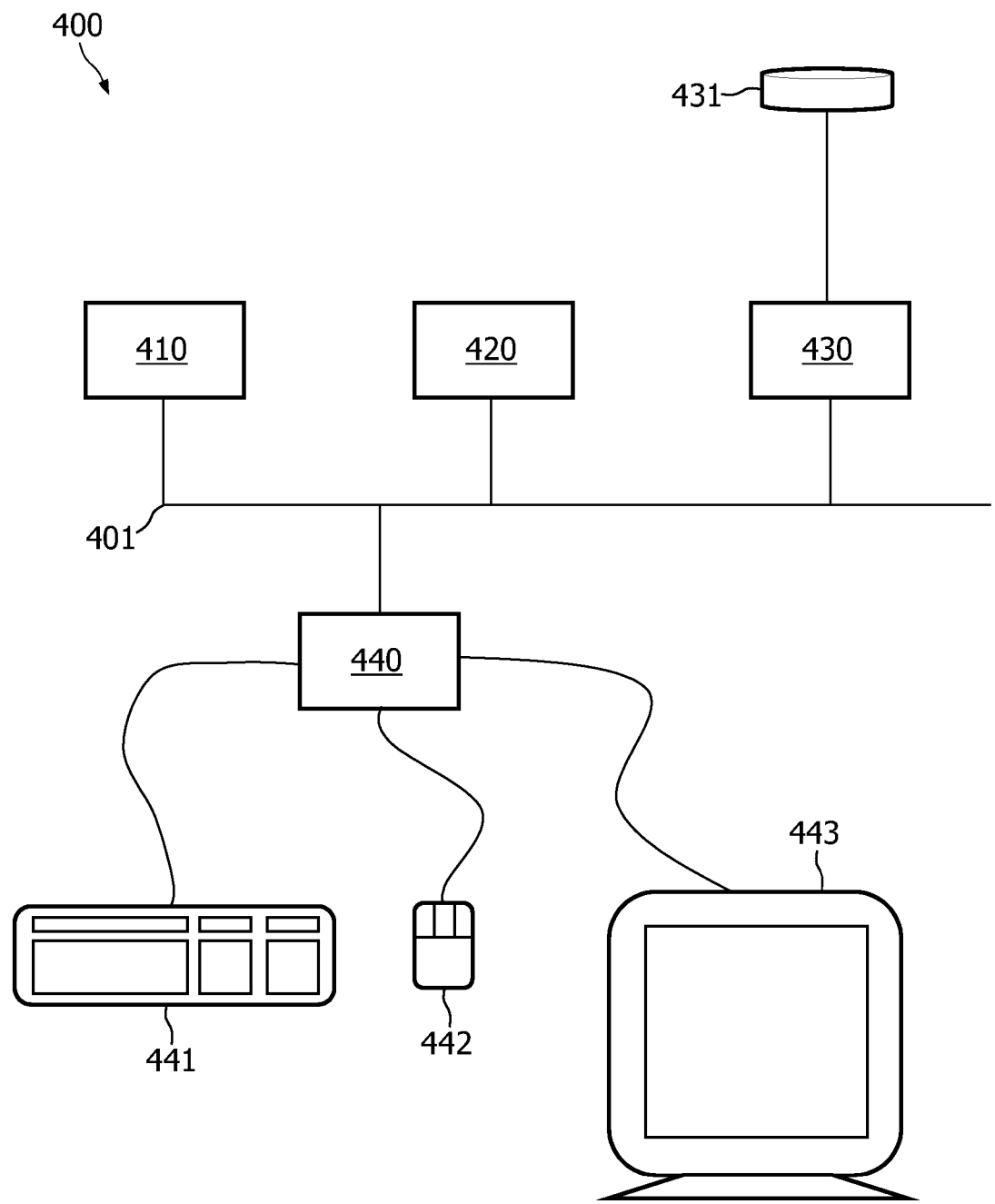
FIG. 4 schematically shows an exemplary embodiment of the workstation.

FIG. 4 schematically shows an exemplary embodiment of the workstation 400. The workstation comprises a system bus 401. A processor 410, a memory 420, a disk input/output (I/O) adapter 430, and a user interface (UI) 440 are operatively connected to the system bus 401. A disk storage device 431 is operatively coupled to the disk I/O adapter 430. A keyboard 441, a mouse 442, and a display 443 are operatively coupled to the UI 440. The system 100 of the invention, implemented as a computer program, is stored in the disk storage device 431. The workstation 400 is arranged to load the program and input data into memory 420 and execute the program on the processor 410. The user can input information to the workstation 400, using the keyboard 441 and/or the mouse 442. The workstation is arranged to output information to the display device 443 and/or to the disk 431. The skilled person will understand that there are numerous other embodiments of the workstation 400 known in the art and that the present embodiment serves the purpose of illustrating the invention and must not be interpreted as limiting the invention to this particular embodiment.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by means of hardware comprising several distinct elements and by means of a programmed computer. In the system claims enumerating several units, several of these units can be embodied by one and the same item of hardware or software. The usage of the words first, second and third, et cetera, does not indicate any ordering. These words are to be interpreted as names.

The invention claimed is:

1. A system that retrieves a volumetric image data subset comprised in data storage of volumetric image data sets, the system comprising:

a first query hardware unit that composes a first query that searches the data storage for a volumetric image data set comprising the volumetric image data subset;

a second query hardware unit that composes a second query that searches the volumetric image data set for the volumetric image data subset, the second query comprising anatomical structure information that identifies an anatomical structure within the volumetric image data set;

a first determination hardware unit that determines the volumetric image data set based on the first query;

a second determination hardware unit that determines the volumetric image data subset of the volumetric image data set based on the anatomical structure identified within the volumetric image data set using the anatomical structure information comprised in the second query;

a segmentation hardware unit that adapts a mesh of a shape model to identify the anatomical structure within the volumetric image data set and segments the identified anatomical structure from the volumetric data set; and a retrieval hardware unit that retrieves the segmented anatomical structure.

2. The system as claimed in claim 1 further comprising an addition unit that adds a new volumetric image data set to the data storage.

3. The system as claimed in claim 2 wherein the second query unit identifies the anatomical structure in the new volumetric image data set based on the anatomical structure information when the new volumetric image data set is added to the data storage.

4. The system as claimed in claim 2, wherein the addition unit obtains reference information for the new volumetric image data set and wherein the reference information is added with the new volumetric image data set to the data storage.

5. The system as claimed in claim 1 wherein the second determination unit determines the volumetric image data subset based on the shape model adapted to the anatomical structure within the volumetric image data set.

6. The system as claimed claim 1 wherein the anatomical structure information further comprises information on a property of the anatomical structure.

7. The system as claimed in claim 1 wherein the retrieval unit retrieves a characteristic of the determined volumetric image data subset.

8. The system as claimed in claim 1 further comprising a client unit comprising the first query unit and the second query unit, and a server unit comprising the data storage, the first determination unit, and the second determination unit.

9. The system as claimed in claim 1, wherein the first query unit, the second query unit, the first determination unit, the second determination unit, and the retrieval unit are part of an image acquisition apparatus.

10. The system as claimed in claim 1, wherein the first query unit, the second query unit, the first determination unit, the second determination unit, and the retrieval unit are part of a workstation.

11. The system as claimed in claim 1 further comprising:
a control unit for receiving control data and providing the control data to the a first query unit, a second query unit, a first determination unit, a second determination unit, a retrieval unit, or a combination thereof.

12. The system as claimed in claim 1, wherein the first query and second query are part of a single query.

13. The system as claimed in claim 1, wherein the first query and second query are not part of a single query.

14. The system as claimed in claim 1, where the volumetric image data set is determined before the second query is composed.

15. The system as claimed in claim 14, wherein the first determination unit identifies reference information of the volumetric image data set, extracts a clue from the reference information, and passes the clue to a user interface, wherein the user interface discloses the clue in a manner to assist with semantically creating the second query.

16. The system as claimed in 14, wherein the first determination unit identifies reference information of the volumetric image data set, extracts a clue from the reference information, and passes the clue to a user interface, wherein the user interface discloses the clue in a manner to assist with refining the first query.

17. The system as claimed in claim 1, where the first determination unit finds a memory address of the volumetric image data set and passes the memory address to the second determination unit.

18. A method of retrieving a volumetric image data subset comprised in data storage of volumetric image data sets, the method comprising:
determining a volumetric image data set based on a first query, where the first query searches the data storage for a volumetric image data set comprising the volumetric image data subset;
determining a volumetric image data subset of the volumetric image data set based on an anatomical structure identified within the volumetric image data set using an anatomical structure information comprised in a second query that searches the volumetric image data set for the volumetric image data subset, wherein the second query comprises anatomical structure information that identifies the anatomical structure within the volumetric image data set;
adapting a mesh of a shape model to identify the anatomical structure within the volumetric image data set;
segmenting the identified anatomical structure from the volumetric data set; and
retrieving the segmented anatomical structure.

19. A computer memory storing a computer program product that is loaded with instructions for retrieving a volumetric image data subset comprised in data storage of volumetric image data sets, the computer program product, when executed by a computer processor, causes the computer processor to carry out the tasks of:
composing a first query that searches the data storage for a volumetric image data set comprising the volumetric image data subset;
composing a second query that searches the volumetric image data set for the volumetric image data subset, the second query comprising anatomical structure information for identifying an anatomical structure within the volumetric image data set;
determining the volumetric image data set based on the first query;
determining the volumetric image data subset of the volumetric image data set based on the anatomical structure identified within the volumetric image data set using the anatomical structure information comprised in the second query;
adapting a mesh of a shape model to identify the anatomical structure within the volumetric image data set;
segmenting the identified anatomical structure from the volumetric data set; and
retrieving the determined volumetric image data subset.

* * * * *